United States Patent [19]

Gustavsson et al.

[11] Patent Number: 4,842,454
[45] Date of Patent: Jun. 27, 1989

[54] METHOD AND AN ARRANGEMENT FOR THE PREPARATION OF INSERT BODIES FOR THE ARTIFICIAL REBUILDING OF TEETH AND HUMAN LIMBS, ETC.

[76] Inventors: Axel G. V. Gustavsson, Gullebovägen 1, S-691 44 Karlskoga; Knut M. G. Andersson, Fack 45, S-830 22, Fåker; Karl E. M. Andersson, Kougstagården, S-830 30 Lit, all of Sweden

[21] Appl. No.: 138,910

[22] PCT Filed: Apr. 23, 1987

[86] PCT No.: PCT/SE87/00194
§ 371 Date: Dec. 23, 1987
§ 102(e) Date: Dec. 23, 1987

[87] PCT Pub. No.: WO87/06451
PCT Pub. Date: Nov. 5, 1987

[30] Foreign Application Priority Data

Apr. 23, 1986 [SE] Sweden ................... 8601870

[51] Int. Cl.[4] ............ B23C 1/18; B23Q 33/00; B23Q 35/18
[52] U.S. Cl. .................... 409/84; 409/100; 409/101; 409/103; 409/104; 409/111; 409/114; 409/127; 409/129
[58] Field of Search ............... 409/84, 98–103, 409/104, 111–114, 127, 129, 126

[56] References Cited

U.S. PATENT DOCUMENTS

| | | | |
|---|---|---|---|
| 2,330,566 | 9/1943 | Edmonds et al. | 409/111 X |
| 2,539,027 | 1/1951 | Marchant | 409/126 X |
| 2,557,876 | 6/1951 | Klema | 409/126 |
| 3,922,950 | 12/1975 | Walter | 409/103 |

FOREIGN PATENT DOCUMENTS 448598 3/1987 Sweden.

*Primary Examiner*—Steven C. Bishop
*Attorney, Agent, or Firm*—Pollock, Vande Sande & Priddy

[57] ABSTRACT

An arrangement is used for the efficient mass production of individual bodies for the artificial rebuilding of teeth, for example. The arrangement comprises a first pair of co-rotating elements, of which the first element (1) is so arranged as to support a replica (21) of a body which is to be produced, and the second element (2) is so arranged as to support a blank from which the body is to be produced. The replica and the blank are caused to rotate synchronously about the axis of rotation (3, 4) of the respective element. In a second pair of elements a third element supports a sensing device (31) which is capable of interacting with the external contour of the replica, and a fourth element supports a tool (52) by means of which the blank is capable of being machined. The first and second pairs of elements are capable of being displaced relative to one another. The fourth element is adjustably connected to the third element (29) in such a way that the tool executes movements which correspond to the shape of the external contour of the replica sensed by the sensing device (31).

10 Claims, 2 Drawing Sheets

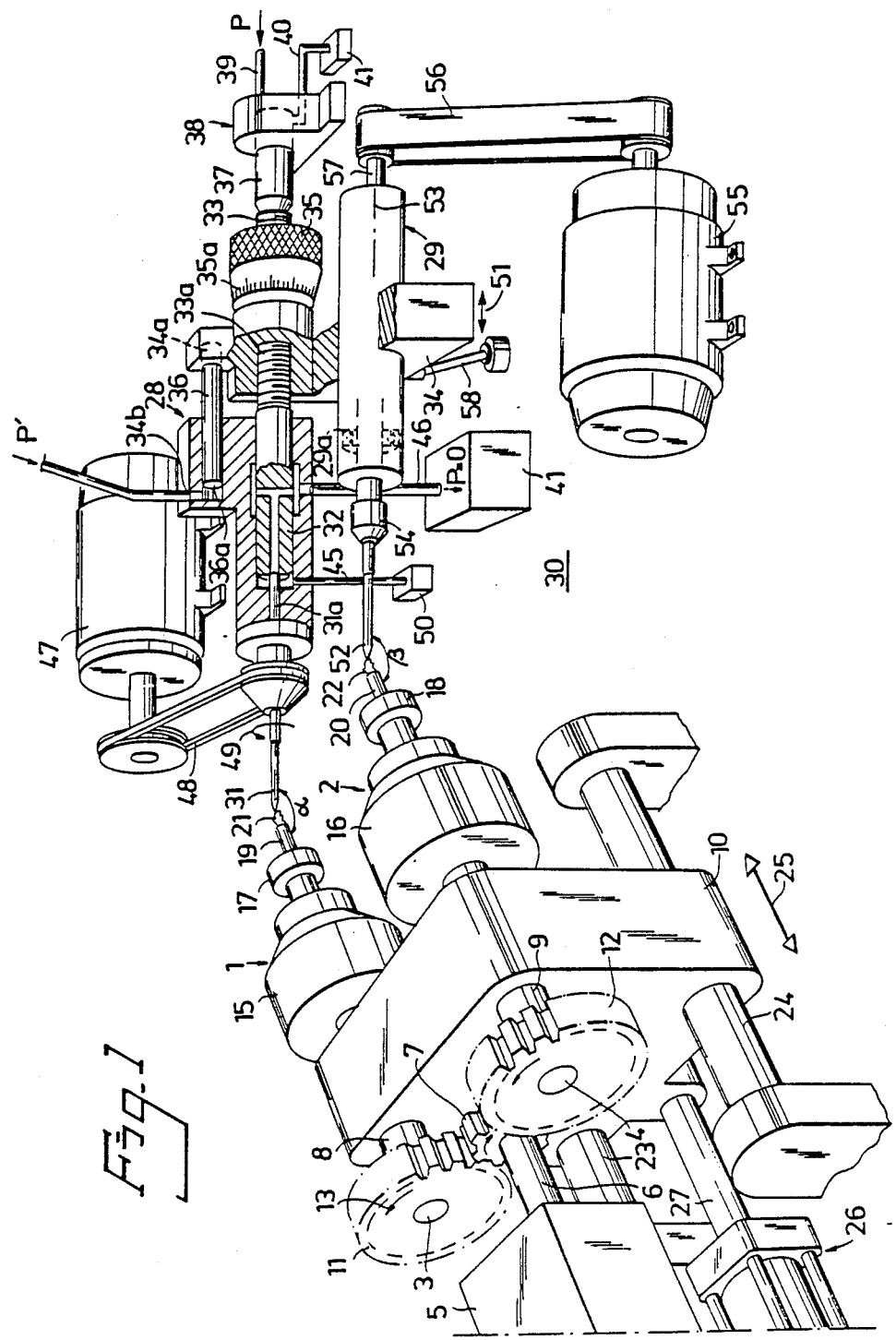

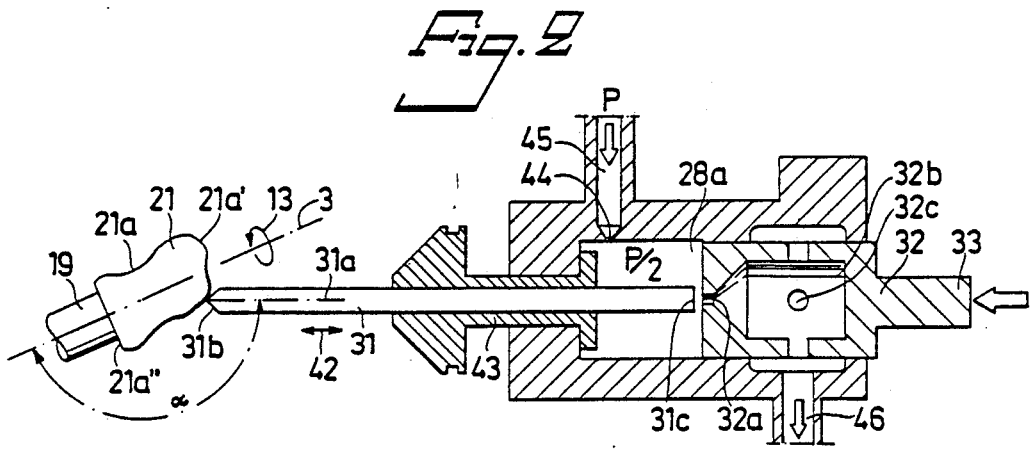
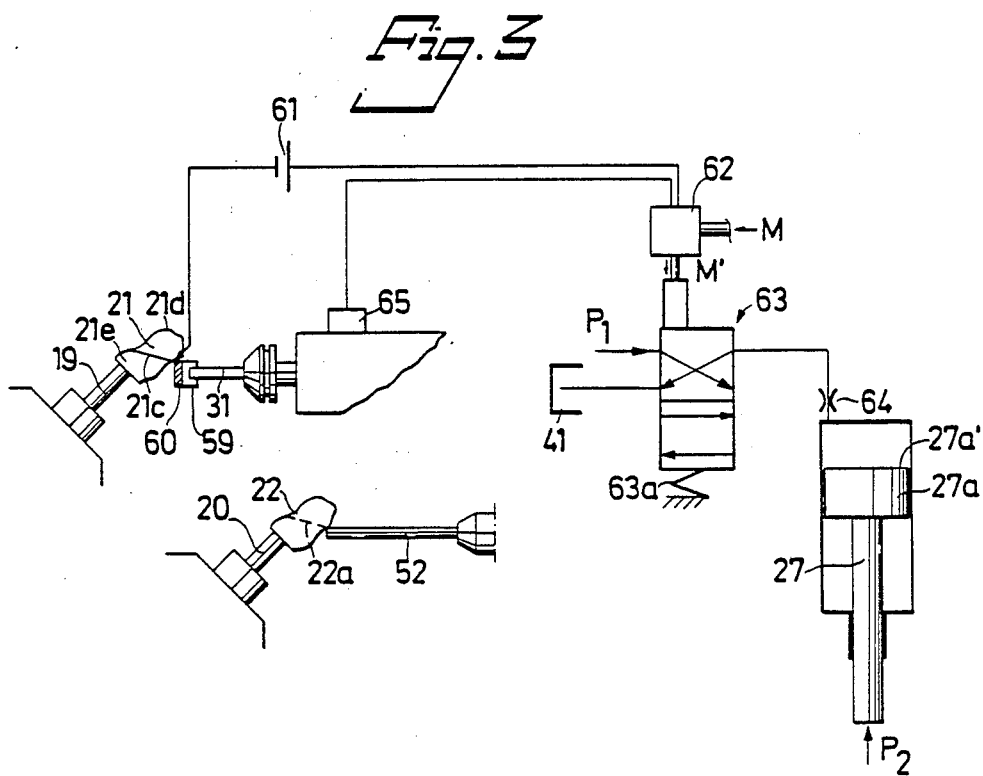

METHOD AND AN ARRANGEMENT FOR THE PREPARATION OF INSERT BODIES FOR THE ARTIFICIAL REBUILDING OF TEETH AND HUMAN LIMBS, ETC.

BACKGROUND OF THE INVENTION

The present invention relates to a method and an arrangement for the production of insert bodies for the artificial rebuilding of teeth and human limbs or equivalent three-dimensional bodies having external contours with different individual characteristic features. The arrangement can also be used in conjunction with supplementary, previously disclosed equipment in order to produce internal contours with characteristic features.

BACKGROUND

The production of metal supporting bodies, for example, for dental crowns, has until now been performed manually by skilled craftsmen. The dentist has used previously disclosed techniques to produce a desired cast impression of the residue(s) of the tooth concerned, whereupon a dental technician has used the cast impression to complete the production process by mechanical means. This previously disclosed procedure was possible provided that castable materials, such as gold, were used for the metal supporting bodies.

The desire to use other materials or alloys in the production of bodies of this kind exists for a variety of reasons. It can be mentioned by way of example, a need to produce metal supporting bodies for dental crowns and supporting bodies for limbs and the like in titanium and other hard materials or alloys.

The production of insert bodies in hard materials is costly to execute due to the fact that each insert body has its own characteristic shape which must be reproduced with comparatively high accuracy.

It is also difficult to solve the problem of the efficient production of insert bodies with individual shapes at relatively low cost.

The present invention has as its object amongst other things to propose an arrangement for the efficient production of bodies of the kind referred to above. In the method according to the present invention, a replica of a body which is to be produced is secured to a first element which, together with a second element, forms part of a first pair of elements. A blank from which the body is to be produced is secured to the second element. The first and second elements are caused to rotate in such a way that the replica and the blank rotate about the axis of rotation of the respective elements. The first pair of elements and a second pair of elements are displaced relative to one another. The second pair of elements contains a third element which supports a sensing device and which is capable of interacting with the external contour of the replica. The second pair of elements also contains a fourth element which supports a tool by means of which the blank is capable of being worked. The fourth element is controlled by the third element in such a way that the tool executes movements which correspond to the shape of the external contour of the replica sensed by the sensing device. The new arrangement is characterized essentially in that, amongst other things, in a pair of co-rotating elements, a first element is so arranged as to support a replica (a cast impression) of a body which is to be produced, and a second element is so arranged as to support a blank form which the body is to be produced, in such a way that the replica and the blank are caused to rotate about the axis of rotation of the respective elements. In a second pair of elements, a third element supports a sensing device which interacts with the external contour of the replica, and a fourth element is so arranged as to support a tool by means of which the blank is capable of being worked. According to further features, the first and second pairs of elements are displaceable relative to one another, and the fourth element is controlled by the third element in such a way that the tool executes movements which correspond to the shape of the external contour of the replica sensed by the sensing device.

According to one embodiment of the present invention the sensing device includes a longitudinally displaceable component part which, through a servo system, provides control of the fourth element and thus of a tool which is capable of interacting with the blank. The servo system may be of a hydraulic or electrical/electronic nature.

The first and second pairs of elements are arranged preferably in such a way that the longitudinal axes of the third and fourth elements face in the direction of the axes of rotation of the first and second elements at obtuse angles, which may preferably be about 135°. In this case the longitudinally displaceable component part of the sensing device and/or its means of support should preferably be imparted with friction-reducing rotation.

In a preferred embodiment the servo system includes a hydraulic piston which is acted upon on either side by fluid pressure. The longitudinally displaceable component part is so arranged in this case, depending on the variation in longitudinal displacement, as to regulate a constriction in the hydraulic piston. In this way the fluid pressure on one side of the piston is varied so a that a differential pressure is created across the piston, producing a corresponding displacement of the fluid piston. In this embodiment, the fluid flow on that side of the fluid piston which is situated on the longitudinally displaceable component part leads from a pressure source initially through a fixed constriction and then through the variable constriction to the inside of the fluid piston which is connectable to a drainage receptacle.

A piston/piston rod connected to the hydraulic pistion or fluid piston can constitute an attachment point for a bearing component which supports the fourth element.

The novel arrangement can be used for the production of the graphite electrode for an electro-erosion apparatus which is used to produce a cavity inside a metal body of the kind in question. The wall of the cavity in this case can be of essentially the same shape as the outside of the metal body, resulting in a hollow, thin-walled and three-dimensional metal body.

The arrangement is also applicable in conjunction with the reduction of the base of the body in accordance with an outline marked by the dentist. The replica is made of or coated with an electrically conducting material to one side of the marked outline, whereas an electrically non-conducting material or coating is used to the other side of the marked outline. The sensing device is thus able to function as an electrical reducing device which, with the help of actuating devices, guides the first and second pairs of elements towards and away from one another depending on whether the reducing device is sensing one side or the other of the marked outline.

The present invention allows accurate production of three-dimensional bodies with individual characteristic features. Efficient production can take place in large quantities and in series with extremely good reproducibility and accuracy.

The arrangement permits considerable freedom of choice with regard to materials, and by the appropriate choice of material the body can be subjected to the necessary accuracy control procedures with regard to its dimensions. In the particular case of three-dimensional bodies intended for use inside the mouth, it is possible to use a material, such as titanium, which is resistant to corrosion by the fluids in the mouth and has no adverse biological effect on the tissues.

The use of the novel arrangement is particularly advantageous in those cases in which the metal bodies are to be provided with cavities. The cavity can be produced by a previously known method by the use of electro-erosion apparatus with an appropriate electrode, for example made of graphite. This electrode is given an external form which corresponds to the external form of the body with its individual characteristic features. The electrode is manufactured with dimensions which correspond to the external dimensions of the tooth residue. The metal body is given the same external form as the external form of the electrode, although it is made slightly larger in order to permit a wall to be produced in the body. The arrangmenet permits extremely thin-walled bodies to be produced, with wall thicknesses of, for example, 0.6–0.7 mm. The wall thickness may vary within a wide range, however.

The present invention arrangement also permits the body to be cut off along a marked outline. This is of very great significance in those cases which involve production of hollow bodies for use as supports in dental crowns. The interface between the support and the tooth residue is critical in this case and calls for a precisely shaped and extremely thin, sharp edge.

DESCRIPTION OF THE DRAWINGS

A preferred embodiment of a method and an arrangement which exhibit the significant characteristic features of the invention is described below with reference to the accompanying drawing, in which:

FIG. 1 shows in perspective view the most important component parts of the arrangement for the invention;

FIG. 2 shows in longitudinal section the function of a longitudinally displaceable component part contained in the arrangement according to FIG. 1; and FIG. 3 shows in the form of a basic diagram the manner in which the arrangement is used for the purpose of shaping the lower edge of a three-dimensional body.

DESCRIPTION OF THE PREFERRED EMBODIMENT AND; BEST MODE OF CARRYING OUT THE INVENTION

A first pair of elements is represented in FIG. 1 by a first element 1 and a second element 2. The elements 1, 2 are rotatable about their respective axes of rotation 3 and 4. Their rotation is achieved with the help of a motor, for example a hydraulic motor, which is provided on its drive shaft 6 with a toothed driving wheel 7. The elements 1 and 2 are provided with bearing shafts 8 and 9 by means of which the elements are supported in a bearing housing 10 in a previously disclosed fashion, for example on ball bearings. The bearing shafts are provided with toothed wheels 11 and 12 which are in engagement with the driving wheel 7 of the motor 5, which driving wheel thus causes the elements 1 and 2 to rotate in the same direction 13 and 14. The toothed wheels are also arranged in such a way that the elements 1 and 2 rotate in synchronism.

The elements 1 and 2 are provided with clamping devices (chucks) 15 and 16 to enable holders 17 and 18 to be secured to the elements. The holders are intended to secure supporting devices 19 and 20 for a three-dimensional body 21, the external contour of which is to be reproduced, and a blank 22 from which the three-dimensional body is to be made in, for example, titanium or a metal alloy, etc. The three-dimensional replica body and the blank are attached to their supporting devices 19 and 20 with the help of an adhesive and/or joining devices and the like, and the supporting devices are retained in the holding devices by a previously disclosed clamping principle. The housing 10 is mounted on guides 23 and 24 so that the elements 1 and 2 are capable of longitudinal displacement along their axes of rotation 3 and 4 in directions indicated by the arrows 25. The longitudinal displacement is achieved with the help of a longitudinal displacement device 26, for example a hydraulic cylinder, the piston 27 of which is attached to the housing 10. The rate of longitudinal displacement is adapted to suit the particular manufacturing operation.

A second pair of elements contains a third element 28 and a fourth element 29. The third element 28 is securely arranged in the frame of the arrangement, which is symbolized by the designation 30 but is not specifically illustrated. The expression 'third element' shall be understood in its widest sense in this context and may be regarded as constituting an integral part of the frame of the arrangement.

The third element constitutes a bearing component for a sensing device 31 which is capable of movement in relation to the frame of the third element. In the illustrative embodiment shown here, the device 31 has the form of a pin (needle) so arranged for longitudinal displacement in the third element. The third element also provides support for a hydraulic piston 32 which is capable of longitudinal displacement and which acts as a servo piston in accordance with the following. An attachment 34 is arranged on a piston rod 33 belonging to the servo piston. The piston rod 33 is provided with an external thread 33a, onto which the attachment can be screwed through a matching internal thread in a transcurrent hole for the piston rod 33.

Also arranged on the thread 33a of the piston rod is a nut 35 or similar which is rigidly anchored to the piston rod in such a way that the piston/piston rod can displaced longitudinally by hand by means of the nut 35 or similar relative to the attachment (or vice versa). The nut 35 is provided with a scale 35a, by means of which the mutual displacement between the attachment and the piston rod can be determined. A rod 36 is supported in such a way as to be capable of longitudinal displacement in a corresponding hole in the third element 28 and is anchored at its one end to the attachment 34 in a hole 34a in the latter. The end surface 36a of the rod is exposed to an actuating pressure P' which can be applied temporarily. With the help of the pressure P' the attachment 34 can be forced backwards relative to the element 28. This function can be utilized in the course of manufacture when the body is finished and when it is accordingly wished to withdraw the needle 31 and the tool 52 in a rearward sense away from the bodies 21 and 22. The pressure P' is applied via an inlet 34b in the attachment. In one embodiment the pressures P' and P are counterbalanced so that the attachment 34 assumes the desired relative position to the element 28. In another embodiment it is possible to make use of stop devices which limit the degree of insertion of the rod 36 into the element 28 by means of the pressure P. The pressure P' can be applied in this way by the 'on-off' principle.

At its end which faces away from the frame of the element 28, the piston rod 33 is capable of interacting with a counter-pressure piston 37 which is supported and force-operated in a bearing housing 38. The counter-force is produced with the help of a hydraulic pressure P in a fluid which is supplied to a connection line 39. A drainage line is indicated by the designation 40, and the drainage tank is represented by 41. The pin 31 is provided with a supporting component 43 which is supported in sliding bearings in the frame of the third element.

The mounting and the function of the pin are illustrated in more detail in FIG. 2. The front end 31b of the pin is capable of interacting with the external contour 21a of the replica 21. During the sensing operation the pin 31 will describe reciprocating longitudinal displacement movements as shown by the arrows 42. The supporting device for the pin 31 is indicated by the designation 43. The other end 31c of the pin extends into a hole 28a for the piston 32. The end 31c of the pin is capable of interacting with a constriction or an inlet 32a in the piston 32. The space 28a is connected through a fixed constriction 44 to a pressure line 45 for a fluid, for example hydraulic oil. The inside 32b of the piston consists of a hollow space which is connected to a drainage line 46 through a hole 32c. The piston areas, constrictions and pressures are selected so that the piston 32 is counter-balanced at all times through either side of the piston being acted upon by identical fluid pressure forces. Fluid such as, for example hydraulic oil, is able to flow in this position of equilibrium from the pressure line 45, into the space 28a, through the constriction 32a, into the internal space 32b, and out through the hole 32c to the drainage line. The fluid pressure generated in this way inside the space 28a is counter-balanced by the force from the counter-pressure piston 37 as shown in FIG. 1.

If, in the course of its continuous sensing of the external contour 21a, the pin is displaced in either of the directions 42, the end 31c of the pin will vary the size of the constriction 32a. The fluid pressure will be increased or reduced inside the space 28a. This variation in pressure causes the servo piston 32 to move in either direction 42. The piston will then endeavour to assume the position of equilibrium indicated above at all times.

The pin 31 has its longitudinal axis 31d facing towards the axis of rotation 3, so that an obtuse angle $\alpha$ is produced. In one preferred embodiment this angle is about 135°. The choice of angle can, however, lie within the range from 90° to approximately 170°. Friction which reduces the sensitivity of the servo system can arise in the bearing 42 in this case. In order to eliminate the major proportion of this friction, the pin and its bearing are caused to rotate about their longitudinal axis 31d, in conjunction with which the direction of rotation is selected in order to achieve the reduction in friction in the bearing 43.

According to FIG. 1, the rotation is achieved with the help of a motor 47 which, through a transmission device, for instance in the form of a belt 48, causes the pin and the bearing to rotate. The speed of rotation of the pin can be 1000 r/min, for example. The direction of rotation is indicated by the designation 49. The pressure tank for the fluid pressure is indicated by the designation 50, and the tank connected to the drainage line 46 is indicated by the designation 41.

The element 29 is rigidly supported in the attachment 43 in such a way that the element 29 follows the movements of the servo piston and the attachment in the directions 51 of longitudinal displacement. The element supports a tool 52 which is capable of interacting with the blank 22 the tool may be in the form of a hard metal milling cutter 52 in the case of a blank made of titanium or some other hard alloy. The longitudinal axis 53 of the element 29 extends in the direction of the longitudinal axis 4 at an angle $\beta$ which should preferably be of the same order of magnitude as the angle $\alpha$. The fourth element is provided with a clamping device (chuck) 54 for the tool 52. The tool is also caused to rotate, which is achieved with the help of a motor 5 and a device for transmitting the movement, in the present case in the form of a belt drive 56. The belt drive is so arranged in this case as to permit the driving of the tool 52 to take place irrespective of the small longitudinal displacement movements which the fourth element 29 executes in the directions 51. The rotation of the tool 52 takes place with the help of the rotatably mounted shaft 57 of the element. The rotatable mounting can be executed in a previously disclosed manner by means of ball bearings 29a. The attachment 34 is secured with the help of one or more supports 58 in such a way that it exhibits torsional resistance.

The mode of operation of the equipment described above is as follows. The first and second elements 1 and 2 are caused to rotate, for example at 1000 r/min, at the same time being displaced towards the pin 31 and the tool 52. During this displacement the pin is able to sense the contour of replica 21 from its top 21a' to its base 21a". Depending on this sensing, the servo piston 32 in the rigidly arranged element 28 is caused to execute longitudinal displacement movements in accordance with the sensing by the pin 31. These movements are transmitted to the attachment 34 and thus to the element 29. The tool 52 accordingly executes a pattern of movements on the blank 22 which correspond to the contour sensed by the pin 31. A three-dimensional body corresponding to the replica 21 will thus be produced from the blank 22. Once the elements 1 and 2 have executed a longitudinal displacement movement which corresponds to the sensing of the pin 31 between 21a' and 21a", the elements can be caused to move in the other direction 25 of longitudinal displacement, and the now finished body can be removed from the element 2 and can be replaced by a new blank, for example in the form of a titanium bar, etc. In order to provide a large unobstructed space around the blank, the needle and the tool, the attachment 34 can be pushed backwards by actuation applied through the surface 36a.

It is possible by the longitudinal adjustment of the attachment 34 relative to the piston rod 33 with the help of the nut 35 easily to achieve different sizes for the external dimensions of the finshed three-dimensional body 22. Adjustments are easily made in this respect in such a way that the external contours of the finished body 22 are larger than, the same as, or smaller than the external contour of the replica 21, for example the individual body with its characteristic features. It is possible in this way to produce a first body with external dimensions which slightly exceed the size of the replica or the cast impression. This first body is executed from the blank selected for the body. It is also possible for a second body to be produced which has the same external contours as the replica or the cast impression. This second body can consist of graphite and can be used as a tool or electrode in an electro-erosion apparatus of a previously disclosed kind.

As shown in FIG. 3, the arrangement can also be used to shape the manufactured body in question at its base. An outline 21b is marked on the replica for this purpose. To that side of the line which contains the top 21d of the replica, the replica is executed with an electrically non-conductive surface coating. To the other side 21e of the line, the replica is electrically conductive. A device 59 which is provided with a part 60 made of an electrically conductive material, but which is otherwise electrically non-conductive, is arranged in such a way as to be capable of being secured to the free end of the needle 31. The part 60 interacts with the external contour of the replica and is connected to a source of electrical energy, for example a battery, to one pole of which the part is connected. The other pole of the energy source or battery is connected to a change-over device 62, for example a solenoid switch, which controls the flow of an actuating fluid M, M' to a two-position valve 63 of the 'on-off' type. In the first position shown in FIG. 3, one side 27a' of the piston 27a of the piston rod 27 is connected to the drainage receptacle 41. In the other position an actuating pressure $P_1$ is connected to the same side 27a' of the piston 27a. The connection to the piston 27a passes through a fixed constriction 64. The change-over device through its electrical winding is also connected to earth (the frame of the arrangement), which is symbolized by the connection component 65.

Through the arrangement described above, the direction of movement of the piston 27a will be varied immediately as the sensing component 60 crosses the marked outline 21c from one area, for example 21d, to the other area, 21e, or vice versa. When the component 60 is in interaction with the electrically conductive component 21e, the circuit is closed via the negative pole of the battery, the component 60, the conductive component 21e of the replica 21, the component 19, the frame of the arrangement, the winding in the device 62 and the positive pole of the battery. The change-over device is activated and causes the valve to move to its second position by means of the actuating fluid M, M'. The pressure $P_1$ is applied to the side 27a' of the piston and produces an actuating pressure on the piston which exceeds a pressure $P_2$ acting continuously on the piston. This causes the replica 21 to move backwards relative to the component 60, which then crosses the marked outline 21c and enters into interaction with the electrically non-conductive material. The circuit is broken, and the effect of the actuating fluid M, M' is interrupted. The valve is returned to its initial position with the help of a return spring 63a. The side 27a' of the piston is connected to the drainage receptacle, and the piston rod is caused to move in its other direction, with the result that the part 21 of the replica is caused to move forwards, and the component 60 again crosses the marked outline 21c and enters into interaction with the electrically conductive material, and so on.

The component part 60 will move with small deflections in such a way as to follow the marking 21c. The tool 52 executes corresponding movements and cuts or grinds away the body 22 along an imaginary line 22a which corresponds to the marking 21c.

The change-over device 62 and the valve 63 can be executed from previously disclosed component parts. The component part 59 can be of cylindrical form and can be applied to the pin 31 in a previously disclosed manner. The component part 60 can have the form of a washer secured, for example by glueing, to the component part 59.

In accordance with the novel method the first and second elements are caused to co-rotate and are displaced relative to the third and fourth elements. The fourth element is controlled by the third element in such a way that the tool is caused to produce the desired machining of the blank. The tool executes a movement which corresponds to the external contour of the replica, in conjunction with which a tooth cap, an entire artificial tooth or a part of an artificial tooth, or some other mechanical body for some other purpose can be produced.

The present invention is not restricted to the embodiment described above by way of example, but may undergo modifications within the scope of the following Patent Claims and the idea of invention. Thus, for example, the valve arrangement for the needle 31 may be executed in a different, previously disclosed manner.

We claim:

1. A method for the production of bodies for the artificial rebuilding of teeth, human limbs or similar three-dimensional bodies having external contours with individual characteristic features, comprising the steps of:
    securing a replica of a body which is to be produced to a first element which, together with a second element, form a first pair of elements which are capable of co-rotating,
    securing a blank from which the body is to be produced to the second element;
    causing the first and second elements to co-rotate in such a way that the replica and the blank rotate about the axes of rotation of the respective elements;
    providing a second pair of elements which includes a third element for supporting a sensing device which is capable of interacting with the external contour of the replica, and a fourth element which supports a tool by means of which the blank is being worked on, with the first and second pairs of elements being displaceable relative to one another;
    controlling said fourth element by the third element in such a way that the tool executes movements which correspond to the shape of the external contour of the replica sensed by the sensing device; wherein
    said sensing device includes a component member movable with respect to a frame of said third element for longitudinal displacement of said component member, said third element further supporting a servo system, by means of which the fourth element and the tool are controlled by the third element for interacting with the blank; and
    wherein the servo system includes a fluid piston which is acted upon on either side by fluid pressure, and said longitudinally displaceable component member is so arranged, as to regulate, depending on the variation in the longitudinal displacement, a first variable constriction in the fluid piston, which together with a fixed constriction, provides variation of the fluid pressure acting on one side of the piston, such that a differential pressure is created across the fluid piston, producing a corresponding displacement of the fluid piston.

2. An arrangement for production of insert bodies for the artificial rebuilding of teeth, human limbs, or similar three-dimensional bodies having external contours with individual characteristic features, comprising:

a first pair of co-rotating elements including a first element for supporting a replica of a body which is to be produced, and a second element for supporting a blank from which the body is to be produced, the replica and the body being rotatable about the axes of rotation of the respective elements; and a second pair of elements including a third element which supports a sensing device capable of interacting with the external contour of the replica, and a fourth element supporting tool by means of which the blank is being worked on, said first and second pairs of elements being displaceable relative to one another, said fourth element being controlled by said third element in such a way that the tool executes movements which correspond to the shape of the external contour of the replica sensed by the sensing device, said sensing device including a component member movable with respect to a frame of said third element for longitudinal displacement of said component member, said third element further supporting a servo system, by means of which the fourth element and the tool are controlled by the third element for interacting with the blank; and wherein the servo system includes a fluid piston which is acted upon on either side by fluid pressure, and said longitudinally displaceable component part is so arranged as to regulate, depending on the variation in the longitudinal displacement, a first variable constriction in the fluid piston, which together with a fixed constriction, provides variation of the fluid pressure acting on one side of the piston, such that a differential pressure is created across the fluid piston, producing a corresponding displacement of the fluid piston.

3. An arrangement according to claim 2, wherein the longitudinal axes of the third and fourth elements face in the direction of the axes of rotation of the first and second elements at obtuse angles, said angles being in the range of from about 90° to about 170°.

4. An arrangement according to claim 3, wherein said angles are about 135°.

5. An arrangement according to claim 2, wherein the movable longitudinally displaceable component member is imparted with friction-reducing rotation.

6. An arrangement according to claim 2, wherein the fluid flow on that side of the fluid piston which faces the longitudinally displaceable component member leads, from a pressure source through the fixed and variable constrictions to the inside of the fluid piston, which is connected to a drainage receptacle.

7. An arrangement according to claim 2, wherein a piston rod which is a part of the servo system provides an attachment point for a bearing component supporting the fourth element.

8. An arrangement according to claim 2, wherein the same replica is usable for producing at least two bodies, a first body having a size larger than that of the replica and being produced from a first blank made of metal or a metal alloy, and a second body having a size corresponding to the external contour of the replica and being produced from a second blank made of electrode material, and wherein by relative positioning of the tool in relation to the blank, a difference in size is achieved between the first and the second bodies, such that the second body is smaller than the first body, and wherein the second body is used as an electrode for the spark-machining of the first body to produce the first body in a hollow form with a wall thickness being controlled by the relative positioning of the tool.

9. An arrangement according to claim 2, wherein, for the purpose of reducing the base of the produced body in accordance with a marked outline, the replica is electrically conductive to one side of the marked outline and is electrically non-conductive to the other side of the marked outline, and wherein the sensing device functions as an electrical reducing device which guides the first and second pairs of elements towards and away from one another depending on whether the reducing device is sensing one side or another.

10. An arrangement according to claim 2, wherein the third element is fixedly positioned with respect to the other elements, wherein the first and second elements are displaceable towards and away from the third and fourth elements, and wherein the sensing device is movable with respect to the fixed third element and controls the movement of the fourth element by means of the servo system.

* * * * *